United States Patent [19]
Whisler

[11] Patent Number: 5,058,592
[45] Date of Patent: Oct. 22, 1991

[54] ADJUSTABLE MOUNTABLE DOPPLER ULTRASOUND TRANSDUCER DEVICE

[76] Inventor: G. Douglas Whisler, 17026 33rd Ave. S.W., Seattle, Wash. 98166

[21] Appl. No.: 608,247

[22] Filed: Nov. 2, 1990

[51] Int. Cl.$^5$ ............................................. A61B 8/00
[52] U.S. Cl. ..................... 128/661.07; 128/DIG. 15; 128/802; 128/662.03; 128/662.04
[58] Field of Search ................. 128/662.03, DIG. 15, 128/802, 775, 662.04, 660.01, 661.07

[56] References Cited

U.S. PATENT DOCUMENTS

| | | | |
|---|---|---|---|
| 4,239,046 | 12/1980 | Ong | 128/DIG. 15 |
| 4,860,768 | 8/1989 | Hon et al. | 128/775 |
| 4,898,177 | 2/1990 | Takano et al. | 128/662.03 |
| 4,920,966 | 5/1990 | Hon et al. | 128/775 |
| 4,947,853 | 8/1990 | Hon | 128/802 |
| 4,947,865 | 8/1990 | Hon et al. | 128/775 |

*Primary Examiner*—Francis Jaworski
*Assistant Examiner*—George Manuel
*Attorney, Agent, or Firm*—Robert W. Becker & Associates

[57] ABSTRACT

An adjustable, mountable Doppler ultrasound transducer device is provided. The device comprises a ring segment for placement on a patient, and a transducer segment that is movably mounted on the ring segment and is provided with electrical leads for connecting the transducer segment to a Doppler instrument. In order to be able to adjust the position of the transducer segment relative to the ring segment, and hence to the body of a patient, the ring segment and the transducer segment have cooperating fasteners, for example in the form of a Velcro fastener.

6 Claims, 2 Drawing Sheets

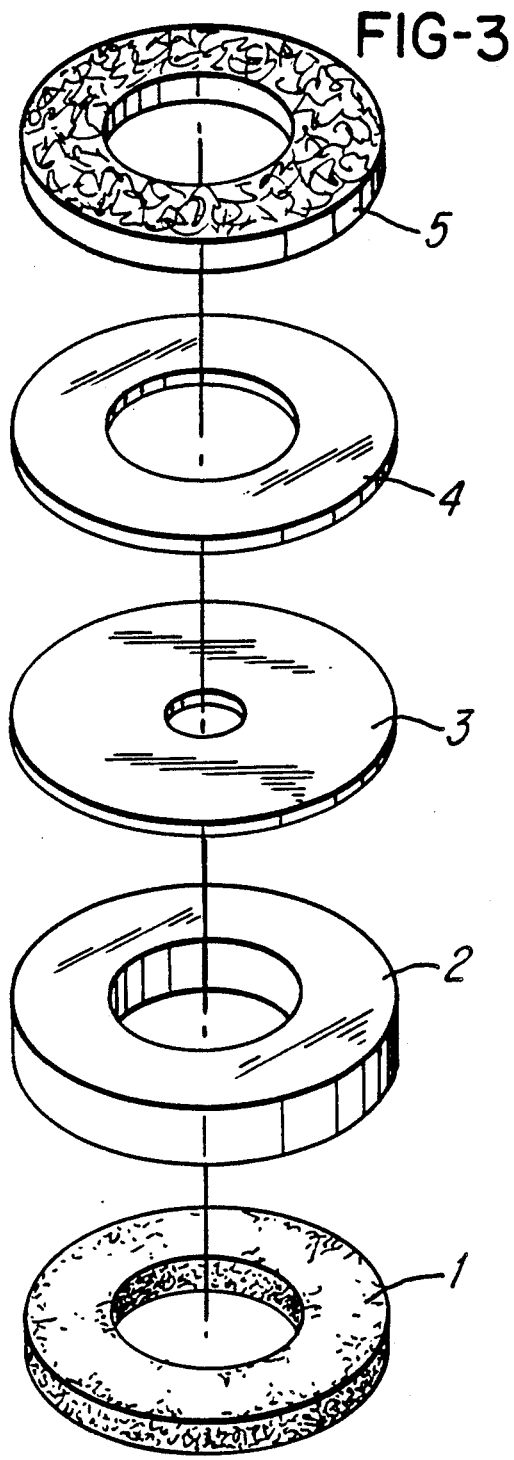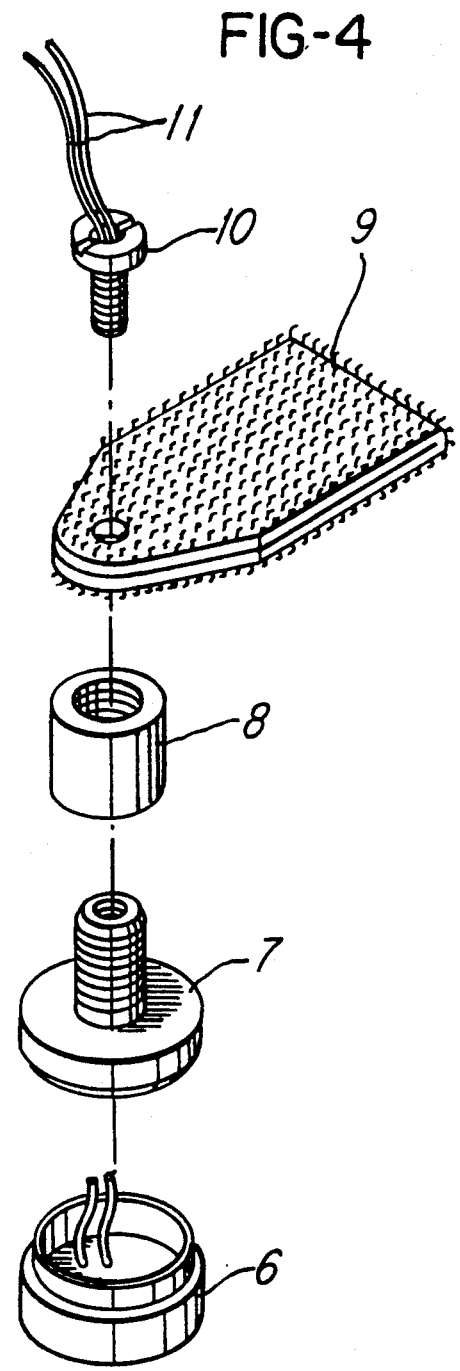

ADJUSTABLE MOUNTABLE DOPPLER ULTRASOUND TRANSDUCER DEVICE

BACKGROUND OF THE INVENTION

The present invention relates to an adjustable, mountable Doppler ultrasound transducer device, especially to facilitate the continuous monitoring of blood flow velocity in human subjects.

Doppler ultrasound is commonly used for the non-invasive detection of fluid flow in human vessels, and for the diagnosis of blood flow disorders in all parts of the body. For example, during certain Doppler ultrasound procedures it is desirable to continuously monitor blood flow signals from a patient for extended periods of time. One such procedure is during the evaluation of the basil cerebral arteries with transcranial Doppler (TCD) ultrasound (Ringlestein, E.B., Transcranial Doppler Monitoring, chapter 10 in Transcranial Doppler Sonography, Aaslid, R. editor, Springer-Verlag 1986.). TCD, which was first described by Aaslid in 1982 (Aasilid, R., Markwalder, T., Nornes, H., Non-Invasive Transcranial Doppler Ultrasound Recording of Flow Velocity of Basal Cerebral Arteries, J. Neurosurgery, 57:1982, 769-774.), uses low frequency ultrasound directed through the intact cranium to detect and display the blood flow velocity and hemodynamics of the circle of Willis and its branches. Recent experience with TCD indicates a need for continuous monitoring of the cerebral circulation during certain surgical procedures that interrupt the normal hemodynamics of the circle of Willis. Carotid endartorectomy and heart valve replacement surgery are examples of surgical procedures where continuous TCD monitoring is useful.

Continuous monitoring is also helpful, for example, in numerous preoperative as well as postoperative situations, as well as in intensive care arenas, and anywhere else where a patients condition should be constantly monitored.

In an attempt to meet this need, U.S. Pat. No. 4,556,066, Semrow, discloses an ultrasound acoustical coupling pad that is secured to a patient's body and that retains a transducer. However, there is still a need for a simple and economical mountable Doppler ultrasound transducer device that can be steered, i.e. where the position of the transducer proper can be varied relative to the body of a patient.

It is therefore an object of the present invention to provide a relatively small, lightweight, and inexpensive mountable Doppler ultrasound transducer device, the position of which relative to the body can be altered in a rapid and straightforward manner.

BRIEF DESCRIPTION OF THE DRAWINGS

This object, and other objects and advantages of the present invention, will appear more clearly from the following specification in conjunction with the accompanying schematic drawings, in which:

FIG. 3 is an exploded view of the ring segment of FIG. 2; and

FIG. 4 is an exploded view of the transducer segment of FIG. 2.

SUMMARY OF THE INVENTION

Figure 1:
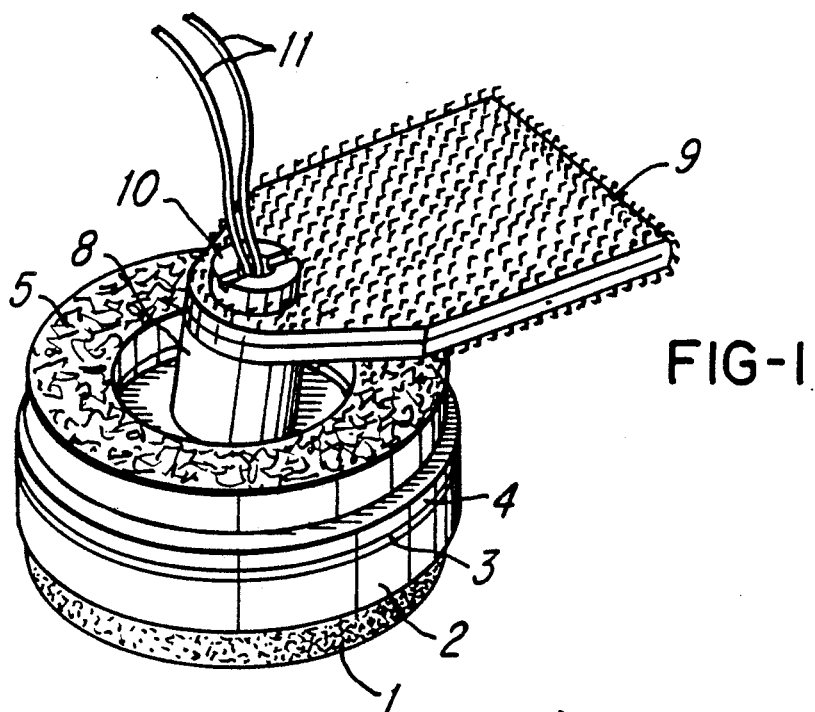
FIG. 1 is a perspective view of one exemplary embodiment of the inventive Doppler ultrasound transducer device.

The adjustable, mountable Doppler ultrasound transducer device of the present invention is characterized primarily by a ring segment that is adapted to be placed on a patient, and a transducer segment that is movably mounted on the ring segment and is provided with electrical leads for connecting the transducer segment to a Doppler instrument, with the ring segment and the transducer segment having cooperating adjusting means for selective adjustment of the position of the transducer segment relative to the ring segment, thereby making it possible to vary the position of the transducer segment relative to the body of a patient. The cooperating adjusting means are preferably in the form of a hook and loop type fastening means, in other words, a Velcro fastening means. Of course, any other suitable fastening means could also be used, although a Velcro fastener provides an inexpensive means for providing an infinite number of fastening positions The inventive device has numerous advantages. One is its compact size, which incorporates a low profile design (with a vertical height of approximately 10mm) and a surface area of approximately 25cm$^2$. This small compact design reduces the risk of inadvertent disruption of the transducer probe position by the surgeon during surgical procedures on the head or neck. A high-tack self adhesive surface is utilized to attach the inventive device directly to the body, i.e. the skin, of a patient, thereby holding the device firmly in position and eliminating the need for a head frame assembly or elastic straps. Where bilateral monitoring is required, two of the inventive devices can be independently placed on both temporal regions without interference from a head frame or elastic straps. In patients having extremely flaccid skin, a lightweight strap (placed over the dome of the cranium) can be used to connect and support the two devices. The inventive device is of lightweight construction. Weight is, of course, an important factor due to the variance in tone or flaccidity of the skin. Heavier devices succumb easily to the forces of gravity, thereby misaligning the desired signal of the transducer portion and necessitating repositioning of the device. The inventive device solves the weight problem by being comprised of lightweight plastic, closed cell foam, small amounts of epoxy resins, and miniaturized electronic components. The weight of the inventive device has been reduced by a factor of 10 relative to conventional designs. One of the most important advantages of the inventive device is that the position of the transducer segment thereof can be altered relative to the ring segment that is placed on the patient, and hence relative to the patient as well. With the inventive device it is possible to steer the transducer and fix the angle of insonation, which is imperative to obtaining and maintaining diagnostic quality signals. This steerability is achieved by providing the transducer signal with, for example, a Velcro tab that can be pressed onto and released from a cooperating Velcro ring of the ring segment. Thus it is possible in a straightforward manner to maintain any desired position and angle of the Doppler transducer segment relative to the ring segment and the body of a patient, with such a maintained position and angle being critical to the quality of the signal. A further advantage is that the inventive device is more economical to use than heretofore known devices, especially because at least part of the ring segment is disposable, whereby the device can be repeatedly reused merely by replacing these inexpensive parts.

Further specific features of the present invention will be described in detail subsequently.

DESCRIPTION OF PREFERRED EMBODIMENTS

Referring now to the drawings in detail, the inventive device comprises two distinct portions, namely a ring segment that is adapted to be placed against the skin of a patient, and a transducer segment that is movably mounted on the ring segment and is connected via electrical leads to a Doppler instrument. These two portions are illustrated in their connected, operational state in FIG. 1, and are shown separated in FIG. 2.

As can be seen particularly clearly from the exploded view of FIG. 3, the ring segment or assembly comprises a closed-cell foam ring 1 that has a self adhesive bottom surface so that the inventive device can be attached directly to the skin of a patient. Such foam ring are known from disposable EKG pads, and an adhesive can be provided thereon that is exposed for use by removing or peeling off a backing sheet or film. The foam ring 1 is laminated to an optional spacer ring 2, which can be made, for example, of PVC. A flexible membrane 3, for example of rubber or some other elastomeric material, is laminated between the plastic spacer 2 and a fixing ring 4, for example of extruded plastic. Attached to the top surface of the fixing ring 4 is a ring 5 of Velcro loop material.

The exploded view of FIG. 4 shows that the transducer or probe segment comprises a probe circuit assembly 6, for example a piezoelectric crystal assembly that contains a miniatured circuit, is enclosed in a PVC housing, and is connected, for example epoxied, to a probe body 7, e.g. of PVC or nylon, with the circuit assembly 6 and the probe body 7 being disposed on the underside of the rubber membrane 3 in the mounted state. A clamping nut 8 e.g. of milled PVC or nylon, is threaded onto a portion of the probe body that extends through the rubber membrane 3, thereby securing the transducer segment to the ring segment. A fastening tab 9 made of Velcro hook material is secured to the clamping nut 8 or the probe body 7 via a hollow screw 10, which can be made of nylon. Probe leads 11 attached to the probe circuit assembly 6 extend through the probe body 7, the clamping nut 8, and the screw 10, and are then adapted to be connected to a non-illustrated Doppler instrument, which in turn is connected to a spectrum analyzer.

Figure 2:
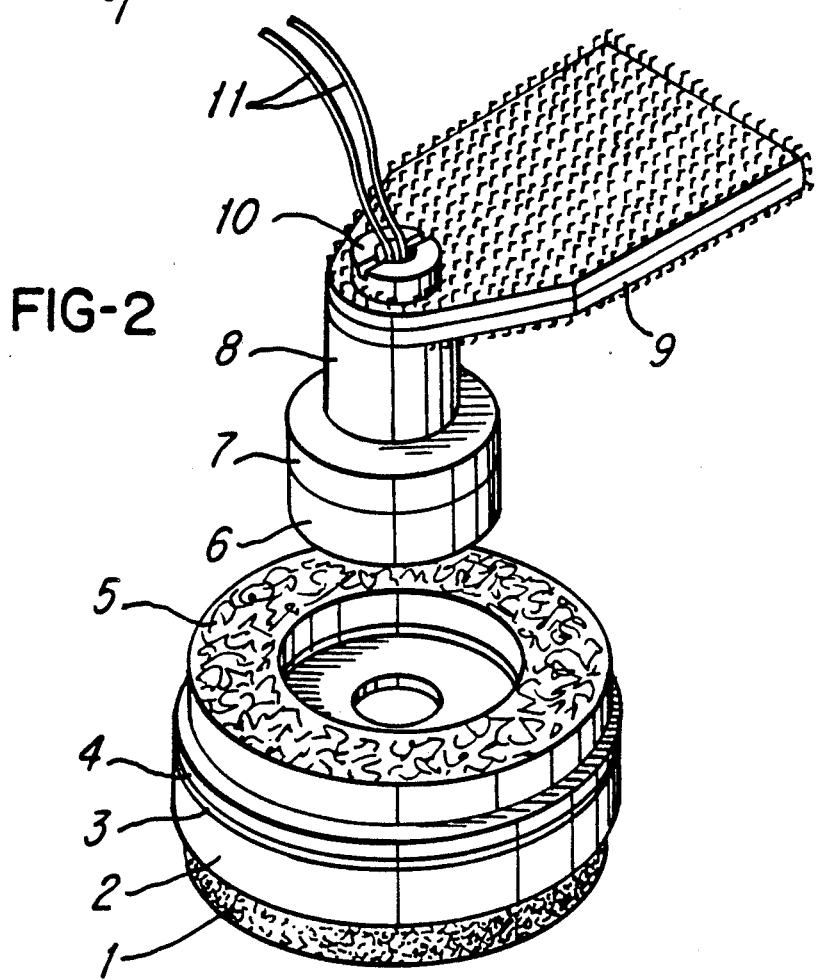
FIG. 2 shows the ring segment and transducer segment of the ultrasound device of FIG. 1 separated from one another.

In the assembled and mounted state illustrated in FIG. 1, the inventive device is ready to be attached to the skin of a patient. This is accomplished by pressing the self adhesive foam ring 1 at the bottom of the device against a patient's skin. This fixes the inventive device on the patient. The position of the transducer segment, comprising the components 6-11, is now ready to be adjusted relative to the ring segment, which comprises the components 1-5. To accomplish this, the Velcro hook material of the fastening tab 9 is pulled or lifted from the Velcro loop material of the ring 5. As a consequence of its attachment to the ring segment via the flexible rubber membrane 3 thereof, the transducer segment can now be pivoted and angled relative to the ring segment so that the transducer segment is properly angled relative to the body of the patient. Once the proper angle and position of the transducer segment, and in particular the probe assembly 6 and body 7 thereof, has been achieved, this angle and position are fixed by pressing the fastening tab 9 onto the Velcro ring 5. Thus, a secure attachment of the transducer segment in a proper position relative to the ring segment is provided. Nonetheless, as a consequence of the cooperating adjusting means provided by the Velcro ring 5 and the Velcro tab 9, the position of the transducer segment relative to the ring segment can at any time be quickly altered as needed for measurement and diagnosis purposes.

The ring segment is inexpensive to produce, so that the inventive device can be economically reused merely by replacing the ring segment or parts thereof as required. It should also be noted that the fixing ring 4 could be disposed between the flexible membrane 3 and the spacer ring 2, to which it could be connected, for example, by a bayonette-type closure.

With regard to the fastening tab 9, the Velcro hooks are illustrated as being on both sides because such a tab is easy to produce by merely folding over a piece of Velcro. However, it is to be understood that the Velcro need only be provided on the underside of the tab so as to be able to cooperate with the loops of the ring 5. In such a case, a piece of Velcro hook material can be disposed on the underside of a carrier material to form the tab 9.

Although in the illustrated embodiment the cooperating fastening means of the ring segment and transducer segment has been described as being in the form of a Velcro fastening means, any other suitable fastening means could also be used, including snap-type or even magnetic connections.

The present invention is, of course, in no way restricted to the specific disclosure of the specification and drawings, but also encompasses any modifications within the scope of the appended claims.

What I claim is:

1. An adjustable, mountable Doppler ultrasound transducer device, comprising:

a ring segment for placement on a patient; and a transducer segment that is movably mounted on said ring segment and is provided with electrical leads for connecting said transducer segment to a Doppler instrument, with said ring segment and said transducer segment having cooperating adjusting means for selective adjustment of the position of said transducer segment relative to said ring segment, with said cooperating adjusting means comprising hook and loop type fastening means that includes a first fastener element connected to said ring segment, and a second fastener element connected to said transducer segment, and whereby said ring segment comprises: a first ring for placement on said patient; said first fastener element in the form of a Velcro ring; and a flexible membrane that is disposed between said first ring and said Velcro ring, with said transducer segment being mounted on said flexible membrane.

2. A device according to claim 1, in which said transducer segment comprises: probe means disposed on a first side of said flexible membrane in said first ring; and, disposed on a second, opposite side of said flexible membrane, said second fastener element in the form of a Velcro tab, with said electrical leads extending from said probe means and through said flexible membrane, said Velcro ring, and said Velcro tab.

3. A device according to claim 2, in which said transducer segment is detachably mounted on said flexible membrane of said ring segment.

4. A device according to claim 3, in which said first ring is a closed-cell foam ring that is provided with a self adhesive surface for direct attachment to the skin of said patient.

5. A device according to claim 4, in which said ring segment further includes a spacer ring disposed between said foam ring and said flexible membrane, with said probe means being disposed in said foam ring and said spacer ring.

6. A device according to claim 4, in which said ring segment further includes a fixing ring disposed between said flexible membrane and said Velcro ring.

* * * * *